United States Patent [19]

Goel

[11] Patent Number: 4,490,550
[45] Date of Patent: Dec. 25, 1984

[54] PREPARATION OF DIBENZOFURAN

[75] Inventor: Anil B. Goel, Worthington, Ohio

[73] Assignee: Ashland Oil, Inc., Ashland, Ky.

[21] Appl. No.: 504,695

[22] Filed: Jun. 15, 1983

[51] Int. Cl.$^3$ ............................................. C07D 307/91
[52] U.S. Cl. .................................................... 549/460
[58] Field of Search ......................................... 549/460

[56] References Cited

U.S. PATENT DOCUMENTS 4,362,883 12/1982 Harvey ................................ 549/460

OTHER PUBLICATIONS

Itatani et al., Chem. & Industry, p. 674 (1971).
Yoshimoto et al., Bull. of Chem. Soc. of Japan, vol. 46, p. 2490 (1973).
Shiotani et al., Angew. Chem., Internat. Ed., vol. 13(7), p. 471 (1974).
Akermark et al., J. Org. Chem. vol. 40, p. 1365 (1975).
Shiotani et al., J.C.S. Perkin I, p. 1236 (1976).

Primary Examiner—Henry R. Jiles
Assistant Examiner—Bernard I. Dentz
Attorney, Agent, or Firm—John F. Jones

[57] ABSTRACT

A process for preparing dibenzofuran by the oxidation of diphenyl ether in the presence of a carboxylic acid and a catalyst composed of a compound of palladium and at least one compound of a member selected from the group consisting of antimony, tin, cobalt, lead, zinc, chromium and potassium is described.

11 Claims, No Drawings

PREPARATION OF DIBENZOFURAN

This invention relates to the manufacture of dibenzofuran from diphenyl ether and more particularly pertains to the selective formation of dibenzofuran by the oxidation of diphenyl ether in the presence of a catalyst composed of a palladium compound and a compound of at least one member selected from the group consisting of antimony, tin, cobalt, lead, zinc, manganese, potassium and chromium.

Dibenzofuran, also known as diphenylene oxide, and its derivatives are useful intermediates for the preparation of dyestuffs, stabilizers for organic materials, and other useful products.

The general commercial availability of dibenzofuran has involved problems of high cost, purity and low yields in its production. Commercially available dibenzofuran is usually obtained from coal tar and often contains impurities such as acenaphthalene and fluorene which cannot be easily removed. Some prior art methods for the production of dibenzofuran are given in Chem. Ind. (London), 674 (1971), Bull. Chem. Soc. Jap., 46, 2490 (1973), Angew Chem. Int. Edn., 13, 471 (1974), J. Org. Chem., 40, 1365 (1975), J. Chem. Soc. Perkin, 1236 (1976), and in recent U.S. Pat. No. 4,362,883. In U.S. Pat. No. 4,362,883 there is described a method for preparing dibenzofuran by reacting diphenyl ether in an oxygen-containing atmosphere in the presence of a palladium carboxylate catalyst, a carboxylic acid and a copper carboxylate promoter or catalyst. Other prior art methods for the preparation of dibenzofuran are disclosed in U.S. Pat. No. 4,362,883, Col. 1, and this disclosure is incorporated herein by reference.

I have discovered an improved process for the preparation of dibenzofuran wherein diphenyl ether is allowed to react at a temperature in the range of from 120° to 250° C. In the presence of molecular oxygen, a carboxylic acid and a catalyst composed of a palladium carboxylate and a carboxylate of at least one member selected from the group consisting of antimony, tin, cobalt, lead, zinc, manganese, potassium and chromium. Preferably, the water formed during the reaction is removed from the reaction mixture as it forms in order to avoid the formation of coupling products such as bi(diphenyl ether), and also to maintain the catalyst activity.

The catalyst can be any carboxylic acid salt of palladium and other metal selected from antimony, tin, cobalt, lead, zinc, manganese, potassium and chromium. Suitable carboxylic acids for the salt can be carboxylic acids having from 2 to 20 carbon atoms. Preferably the carboxylic acids should have from 2–4 carbon atoms.

The carboxylic acid used in the process of my invention which serves as part of the reaction medium can be any carboxylic acid having from 2–20 carbon atoms. Preferably this carboxylic acid should contain 2–14 carbon atoms. The amount of carboxylic acid used in my process can vary over a wide range although it is best to use enough carboxylic acid to make the reaction system homogeneous. Inert organic solvents such as linear and cyclic hydrocarbons can be used in my process as diluents and for the purpose of removing water of reaction azeotropically if desired. Such solvents include hexane, heptane, etc.

The amount of catalyst used in my process can be varied within wide limits although it is usually desirable to use only enough catalyst to provide good reaction rates. Typically, the amount of catalyst will vary between 0.01% and 20% by weight, preferably 0.05% to 5% by weight. Within these ranges it is usually convenient to use molar ratios of palladium to the other metal or metals of from 1:0.1 to 1:20 and preferably from 1:0.2 to 1:10.

The process of my invention can be carried out in any molecular oxygen-containing atmosphere at pressures varying from about atmospheric up to about 10 atmospheres or higher. For convenience it is usually desirable to carry out the reaction at or near ambient pressure.

The oxygen can be used in pure form or it can be diluted with inert diluents such as nitrogen, carbon dioxide, argon, helium, etc. Air is a good source of oxygen for my process.

The reaction temperature can vary from 100° C. to 300° C. but generally a temperature in the range of from 120° C. to 200° C. is preferred.

The time of reaction is not critical and will vary according to the temperature, pressure, catalyst concentration, etc. used as will be apparent to those skilled in the art. Usually reaction times of from a minute or two up to several hours depending upon other reaction conditions are sufficient for producing good conversions of diphenyl ether with good selectivity of dibenzofuran.

The process of my invention can be carried out batch-wise, continuously, or in an intermittent manner and the apparatus needed for these types of reactions are well known to those skilled in the art.

The following Examples will further illustrate my invention.

EXAMPLE 1

A glass reactor equipped with external heater, mechanical stirrer, gas inlet means and a Dean Stark type condenser was used in the oxidative cyclization of diphenyl ether to dibenzofuran. A reaction mixture composed of 333 millimols of octanoic acid, 6 millimols of palladium acetate, 6 millimols of antimony acetate and 58 millimols of diphenyl ether was stirred at a reaction temperature of 160°±5° C. and oxygen was bubbled into the mixture at the rate of 50 to 100 cc/min. during the course of the reaction. Water produced during the reaction was condensed and collected in the Dean Stark apparatus. From time to time or continuously additional diphenyl ether could be introduced into the reaction mixture by pumping. During a reaction period of 5 hours a total of 30 g. (176 m mols) of diphenyl ether was subjected to the oxidation reaction. G.C. analysis of the reaction mixture at the end of the reaction period showed that 116 m mols of dibenzofuran was formed and a conversion of 70% of diphenyl ether had occurred with less than 5% by weight of the coupling product of diphenyl ether being formed.

EXAMPLE 2

The procedure of Example 1 was repeated using a reaction mixture composed of 50 g. (347 m mols) of octanoic acid, 10 g. (59 m mols) of diphenyl ether, 1.34 g. (6 m mols) of palladium diacetate, 1.8 g. (6 m mols) of antimony triacetate, and 5 ml. of n-heptane as solvent. The Dean Stark tube was also filled with heptane at the beginning of the reaction. The reaction was carried out at about 165° C. for one hour under an oxygen flow of 200 cc/min. and water heptane azeotropic distillation was used to collect the water in the Dean Stark tube as it formed in the reaction. G. C. analysis of the reaction mixture at the end of the reaction showed that 31 m mols of dibenzofuran had formed with a 95% selectivity to the diphenyl ether.

EXAMPLE 3

The reaction described in Example 2 was repeated and additional diphenyl ether (10 g., 59 m mols) was introduced into the reaction mixture at a slow rate during the 2 hour reaction period. A total of 20 g. (118 m mols) of diphenyl ether was used in the reaction. Analysis of the reaction mixture after the completion of the 2 hour reaction time showed that 56 m mols of diphenyl ether were converted with a yield of 52 m mols of dibenzofuran.

EXAMPLE 4

The procedure of Example 2 was repeated using 10.3 g. (60.6 m mols) of diphenyl ether. The reaction was carried out for 5 hours. G. C. analysis of the resulting reaction mixture showed nearly complete conversion of the diphenyl ether (greater than 97%) yielding 41 m mols of dibenzofuran and 15 m mols of dibenzofuran octanoate (52% ortho, 30% meta, 18% para).

EXAMPLE 5

The procedure of Example 1 was repeated using 66 g. (330 m mols) of lauric acid instead of octanoic acid and 22.4 g. (132 m mols) of diphenyl ether was used. The reaction was carried out at about 165° C. with 360 ml/min. of oxygen flow for a total of 5 hours. G. C. analysis of the resulting mixture showed the formation of 32 m mols of dibenzofuran.

EXAMPLE 6

The procedure described in Example 2 was followed using a reaction mixture composed of 40 g. (276 millimols) of octanoic acid, 10 g. (59 m mols) of diphenyl ether, 0.15 g. (0.7 m mols) of Pd(OAc)$_2$, 0.26 g. (0.7 m mols) of Pb(OAc)$_2$.3H$_2$O, 0.18 g. (0.7 m mols) of PPh$_3$ and 5 ml. of n-heptane as solvent. The reaction was carried out at about 165° C. using an addition rate of 100 cc/min. of oxygen for a reaction time of one hour. G. C. analysis of the resulting reaction mixture showed that 20% of the diphenyl ether had been converted to 9 m mols of dibenzofuran (88% selectivity).

EXAMPLE 7

The procedure of Example 6 was followed except that 0.15 g. (0.7 m mols) of Zn(OAc)$_2$.2H$_2$O was used instead of the Pb(OAc)$_2$. 3H$_2$O. The analysis of the product showed that 22% of the diphenyl ether was converted producing 10 m mols of dibenzofuran (90% selectivity).

EXAMPLE 8

The procedure of Example 6 was followed except that 0.7 m mols of Co(OAc)$_2$. 4H$_2$O was used instead of the Pb(OAc)$_2$. 3H$_2$O. The reaction was carried out for 3 hours and produced about 18 m mols of dibenzofuran.

EXAMPLE 9

The reaction was carried out as in Example 8 except that 0.7 m mols of Mn(OAc)$_2$ was used instead of Co(OAc)$_2$.4H$_2$O. Analysis of the reaction mixture after 3 hours showed the formation of about 16 m mols of dibenzofuran.

EXAMPLE 10

The procedure of Example 6 was followed using 0.7 m mols of Sb(OAc)$_3$ and 0.7 m mols of Cr(OAc)$_3$.H$_2$O in place of the Pb(OAc)$_2$.3H$_2$O. The reaction produced 11 m mols of dibenzofuran.

EXAMPLE 11

The procedure of Example 10 was followed except that 0.7 m mols of KOAc were used in place of the Cr(OAc)$_3$.H$_2$O. Analysis of the reaction product showed that 8 m mols of dibenzofuran had formed.

I claim:

1. A process for the production of dibenzofuran which comprises reacting diphenyl ether with oxygen in the presence of a carboxylic acid and a catalyst composed of a palladium carboxylate and a carboxylate of at least one member selected from the group consisting of antimony, tin, cobalt, lead, manganese, potassium, zinc and chromium.

2. The process of claim 1 wherein the carboxylic acid is one having from 2 to 20 carbon atoms.

3. The process of claim 2 wherein the catalyst is composed of a palladium carboxylate and an antimony carboxylate.

4. The process of claim 2 wherein the catalyst is composed of a palladium carboxylate and a lead carboxylate.

5. The process of claim 2 wherein the catalyst is composed of a palladium carboxylate and a zinc carboxylate.

6. The process of claim 2 wherein the catalyst is composed of a palladium carboxylate and a cobalt carboxylate.

7. The process of claim 2 wherein the catalyst is composed of a palladium carboxylate and a manganese carboxylate.

8. The process of claim 2 wherein the catalyst is composed of a palladium carboxylate and a chromium carboxylate.

9. The process of claim 2 wherein the catalyst is a palladium carboxylate and a potassium carboxylate.

10. The process of claim 1 wherein there is also included an inert organic solvent.

11. The process of claim 10 wherein the inert organic solvent is heptane.

* * * * *